US008124382B2

(12) United States Patent  
Zhu et al.

(10) Patent No.: US 8,124,382 B2  
(45) Date of Patent: Feb. 28, 2012

(54) METHODS, MICROARRAY, AND KITS FOR DETECTION OF DRUG RESISTANCE GENES IN GRAM-NEGATIVE BACTERIA

(75) Inventors: Lingxiang Zhu, Beijing (CN); Zhiwei Zhang, Beijing (CN); Di Jiang, Beijing (CN); Ning Du, Beijing (CN); Can Wang, Beijing (CN); Huawei Yang, Beijing (CN); Qiong Zhang, Beijing (CN); Huafang Gao, Beijing (CN); Yuxiang Zhou, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 470 days.

(21) Appl. No.: 12/097,237

(22) PCT Filed: Jan. 18, 2007

(86) PCT No.: PCT/CN2007/000199  
§ 371 (c)(1),  
(2), (4) Date: Nov. 21, 2008

(87) PCT Pub. No.: WO2007/082481  
PCT Pub. Date: Jul. 26, 2007

(65) Prior Publication Data  
US 2009/0239758 A1  Sep. 24, 2009

(30) Foreign Application Priority Data  
Jan. 18, 2006  (CN) .......................... 2006 1 0001309

(51) Int. Cl.  
*C12P 19/34* (2006.01)
(52) U.S. Cl. ..................................................... 435/91.2
(58) Field of Classification Search .................. 435/91.2  
See application file for complete search history.

(56) References Cited

U.S. PATENT DOCUMENTS

| | | | |
|---|---|---|---|
| 6,001,564 A | | 12/1999 | Bergeron et al. |
| 6,242,223 B1 | * | 6/2001 | Hanson et al. ............... 435/91.2 |
| 2003/0219749 A1 | * | 11/2003 | Hanson et al. ..................... 435/6 |
| 2006/0210999 A1 | * | 9/2006 | Grimm et al. ..................... 435/6 |

FOREIGN PATENT DOCUMENTS

CN  1635150 A  7/2005

OTHER PUBLICATIONS

Brintrup et al. Biotechnology, vol. 2, No. 2, pp. 121-130, 2003.*  
Abraham, E.P. et al. (1940). "An Enzyme from Bacteria Able to Destroy Penicillin," *Nature* 146:837, re-printed in *Reviews of Infectious Diseases* 10(4):677-678.  
Bauernfeind, A. et al. (1989). "Extended Broad Spectrum β-Lactamase in Klebsiella Pneumoniae Including Resistance to Cephamycin," *Infection* 17:316-321.  
Blanchard, A.P. et al. (1996). "High-Density Oligonucleotide Arrays," *Biosensors & Bioelectronics* 11(6/7):687-690.  
Bush, K. et al. (Jun. 1995). "A Functional Classification Scheme for β-Lactamases and Its Correlation with Molecular Structure," *Antimicrobial Agents Chemotherapy* 39(6):1211-1233.  
Cao, V.T.B. et al. (2000). "Emergence of Imipenem Resistance in *Klebsiella pneumoniae* owing to Combination of Plasmid-Mediated CMY-4 and Permeability Alteration," *Journal of Antimicrobial Chemotherapy* 46:895-900.  
Huang, H. et al. (1995). "Membrane Topology and Site-Specific Mutagenesis of *Pseudomonas aeruginosa* Porin OprD," *Molecular Microbiology* 16(5):931-941.  
Marshall, A. et al. (Jan. 1998). "DNA Chips: An Array of Possibilities, Developers Must Now Move Beyond Technical Wizardry to Meet the Demands of the Market," *Nature Biotechnology* 16:27-31.  
Martínez-Martínez, L. et al. (Jul. 1999). "Roles of β-Lactamases and Porins in Activities of Carbapenems and Cephalosporins Against *Klebsiella pneumoniae*," *Antimicrobial Agents and Chemotherapy* 43(7):1669-1673.  
Maskos, U. et al. (1992). "Oligonucleotide Hybridisations on Glass Supports: A Novel Linker for Oligonucleotide Synthesis and Hybridisation Properties of Oligonucleotides Synthesised in situ," *Nucleic Acids Research* 20(7):1679-1684.  
Masuda, N. et al. (Mar. 1995). "Outer Membrane Proteins Responsible for Multiple Drug Resistance in *Pseudomonas aeruginosa*," *Antimicrobial Agents and Chemotherapy* 39(3):645-649.  
Matson, R.S. et al. (Jan. 1, 1995). "Biopolymer Synthesis on Polypropylene Supports: Oligonucleotdie Arrays," *Analytical Biochemistry* 224(1):110-116.  
Philippon, A. et al. (Jan. 2002). "Plasmid-Determined AmpC-Type β-Lactamases," *Antimicrobial Agents and Chemotherapy* 46(1):1-11.  
Ramsay, G. (Jan. 1998). "DNA Chips: State-of-the-Art," *Nature Biotechnology* 16:40-44.  
Schena, M. et al. (Oct. 1996). "Parallel Human Genome Analysis: Microarray-Based Expression Monitoring of 1000 Genes," *Proc. Natl. Acad Sci. U.S.A.* 93:10614-10619.  
Wahl, G.M. et al. (Aug. 1979). "Efficient Transfer of large DNA Fragments from Agarose Gels to Diazobenzyloxymethyl-Paper and Rapid Hybridization by Using Dextran Sulfate," *Proc. Natl. Acad. Sci. U.S.A.* 76(8):3683-3687.  
Zhou, Q. et al. (2000). "A Molecular Epidemiologic Study on Nosocomial Infection Caused by ESBL Producing Klebsiella pneumoniae," *Chin J. Nosocomiol.* 10(1):10-12. (Translation of Abstract Only).

\* cited by examiner

*Primary Examiner* — Gary Benzion  
*Assistant Examiner* — Cynthia Wilder  
(74) *Attorney, Agent, or Firm* — Morrison & Foerster LLP

(57) ABSTRACT

The present invention provides kits and microarrays containing primer pairs for amplifying drug resistance genes and/or probes for detection of drug resistance genes. Also provided are methods of detecting drug resistance genes using kits and microarrays described herein.

18 Claims, 2 Drawing Sheets

E298  BJ-7  BJ-35

TR3104

Z302

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
ggtttcggat gttacagcgt                                              20

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
cgcccttatt cccttttttg cgg                                          23

<210> SEQ ID NO 3
```

```
<211> LENGTH: 43
<212> TYPE: DNA
<213> ORGANISM: Artificial Sequence
<220> FEATURE:
<223> OTHER INFORMATION: Synthetic Construct

<400> SEQUENCE: 3
ggtttcggat gttacagcgt tcagtgaggc acctatctca gcg          43

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
tcactcaagg atgtattgtg g                                  21

<210> SEQ ID NO 5
<211> LENGTH: 39
<212> TYPE: DNA
<213> ORGANISM: Artificial Sequence
<220> FEATURE:
<223> OTHER INFORMATION: Synthetic Construct

<400> SEQUENCE: 5
ggtttcggat gttacagcgt ttagcgttgc cagtgctcg               39

<210> SEQ ID NO 6
<211> LENGTH: 44
<212> TYPE: DNA
<213> ORGANISM: Artificial Sequence
<220> FEATURE:
<223> OTHER INFORMATION: Synthetic Construct

<400> SEQUENCE: 6
ggtttcggat gttacagcgt ccgtcacgct gttgttagga agtg         44

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
ccttaggttg aggctgggtg aagt                               24

<210> SEQ ID NO 8
<211> LENGTH: 41
<212> TYPE: DNA
<213> ORGANISM: Artificial Sequence
<220> FEATURE:
<223> OTHER INFORMATION: Synthetic Construct

<400> SEQUENCE: 8
ggtttcggat gttacagcgt tgcaacggat gatgttcgcg g            41

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
```

```
cctttgagcc acgtcaccaa c                                              21
```

<210> SEQ ID NO 10
<211> LENGTH: 41
<212> TYPE: DNA
<213> ORGANISM: Artificial Sequence
<220> FEATURE:
<223> OTHER INFORMATION: Synthetic Construct

<400> SEQUENCE: 10

```
ggtttcggat gttacagcgt gctgctcaag gagcacagga t                        41
```

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11

```
cacattgaca taggtgtggt gc                                             22
```

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12

```
ggtttcggat gttacagcgt tggccagaac tgacaggcaa a                        41
```

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13

```
tttctcctga acgtggctgg c                                              21
```

<210> SEQ ID NO 14
<211> LENGTH: 42
<212> TYPE: DNA
<213> ORGANISM: Artificial Sequence
<220> FEATURE:
<223> OTHER INFORMATION: Synthetic Construct

<400> SEQUENCE: 14

```
ggtttcggat gttacagcgt aactttcaca ggtgtgctgg gt                       42
```

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15

```
ccgtacgcat actggctttg c                                              21
```

<210> SEQ ID NO 16
<211> LENGTH: 41
<212> TYPE: DNA
<213> ORGANISM: Artificial Sequence
<220> FEATURE:

<223> OTHER INFORMATION: Synthetic Construct

<400> SEQUENCE: 16
ggtttcggat gttacagcgt aacagcctca gcagccggtt a                41

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
ttcgccgcaa tcatccctag c                                     21

<210> SEQ ID NO 18
<211> LENGTH: 41
<212> TYPE: DNA
<213> ORGANISM: Artificial Sequence
<220> FEATURE:
<223> OTHER INFORMATION: Synthetic Construct

<400> SEQUENCE: 18
ggtttcggat gttacagcgt tcggtaaagc cgatgttgcg g                41

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
cttccactgc ggctgccagt t                                     21

<210> SEQ ID NO 20
<211> LENGTH: 42
<212> TYPE: DNA
<213> ORGANISM: Artificial Sequence
<220> FEATURE:
<223> OTHER INFORMATION: Synthetic Construct

<400> SEQUENCE: 20
ggtttcggat gttacagcgt aacatggggt atcagggaga tg               42

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
caaagcgcgt aaccggattg g                                     21

<210> SEQ ID NO 22
<211> LENGTH: 31
<212> TYPE: DNA
<213> ORGANISM: Artificial Sequence
<220> FEATURE:
<223> OTHER INFORMATION: Synthetic Construct

<400> SEQUENCE: 22
tttttttttt ttcgacgagc gtgacaccac g                          31

<210> SEQ ID NO 23

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 23
tttttttttt ttggaatggc ggtattcagc gta                                    33

<210> SEQ ID NO 24
<211> LENGTH: 31
<212> TYPE: DNA
<213> ORGANISM: Artificial Sequence
<220> FEATURE:
<223> OTHER INFORMATION: Synthetic Construct

<400> SEQUENCE: 24
tttttttttt ttttcgtctc ccagctgtcg g                                      31

<210> SEQ ID NO 25
<211> LENGTH: 32
<212> TYPE: DNA
<213> ORGANISM: Artificial Sequence
<220> FEATURE:
<223> OTHER INFORMATION: Synthetic Construct

<400> SEQUENCE: 25
tttttttttt ttcgccttgt catccagctg ca                                     32

<210> SEQ ID NO 26
<211> LENGTH: 35
<212> TYPE: DNA
<213> ORGANISM: Artificial Sequence
<220> FEATURE:
<223> OTHER INFORMATION: Synthetic Construct

<400> SEQUENCE: 26
tttttttttt ttgctttatc cctaacgtca tcggg                                  35

<210> SEQ ID NO 27
<211> LENGTH: 29
<212> TYPE: DNA
<213> ORGANISM: Artificial Sequence
<220> FEATURE:
<223> OTHER INFORMATION: Synthetic Construct

<400> SEQUENCE: 27
tttttttttt tttgtgatcc ccttccact                                         29

<210> SEQ ID NO 28
<211> LENGTH: 32
<212> TYPE: DNA
<213> ORGANISM: Artificial Sequence
<220> FEATURE:
<223> OTHER INFORMATION: Synthetic Construct

<400> SEQUENCE: 28
tttttttttt tttactcagc gaacccactt ca                                     32

<210> SEQ ID NO 29
<211> LENGTH: 29
<212> TYPE: DNA
<213> ORGANISM: Artificial Sequence
<220> FEATURE:
<223> OTHER INFORMATION: Synthetic Construct

<400> SEQUENCE: 29
```

-continued

```
tttttttttt ttagggaggc gttatccgt                                              29

<210> SEQ ID NO 30
<211> LENGTH: 31
<212> TYPE: DNA
<213> ORGANISM: Artificial Sequence
<220> FEATURE:
<223> OTHER INFORMATION: Synthetic Construct

<400> SEQUENCE: 30
tttttttttt tttagagccc agctcaaaca g                                           31

<210> SEQ ID NO 31
<211> LENGTH: 32
<212> TYPE: DNA
<213> ORGANISM: Artificial Sequence
<220> FEATURE:
<223> OTHER INFORMATION: Synthetic Construct

<400> SEQUENCE: 31
tttttttttt ttcaaggttt gtggagtgac ag                                          32

<210> SEQ ID NO 32
<211> LENGTH: 32
<212> TYPE: DNA
<213> ORGANISM: Artificial Sequence
<220> FEATURE:
<223> OTHER INFORMATION: Synthetic Construct

<400> SEQUENCE: 32
tttttttttt ttcggtgtgg gtcagcgcga tc                                          32

<210> SEQ ID NO 33
<211> LENGTH: 31
<212> TYPE: DNA
<213> ORGANISM: Artificial Sequence
<220> FEATURE:
<223> OTHER INFORMATION: Synthetic Construct

<400> SEQUENCE: 33
tttttttttt ttggctggtt tatcgccgat a                                           31

<210> SEQ ID NO 34
<211> LENGTH: 31
<212> TYPE: DNA
<213> ORGANISM: Artificial Sequence
<220> FEATURE:
<223> OTHER INFORMATION: Synthetic Construct

<400> SEQUENCE: 34
tttttttttt ttcggagctg gccagcgggg t                                           31

<210> SEQ ID NO 35
<211> LENGTH: 31
<212> TYPE: DNA
<213> ORGANISM: Artificial Sequence
<220> FEATURE:
<223> OTHER INFORMATION: Synthetic Construct

<400> SEQUENCE: 35
tttttttttt ttcggagcta gccagcgggg t                                           31

<210> SEQ ID NO 36
<211> LENGTH: 31
<212> TYPE: DNA
<213> ORGANISM: Artificial Sequence
<220> FEATURE:
```

<223> OTHER INFORMATION: Synthetic Construct

<400> SEQUENCE: 36
tttttttttt ttcggagctg cccarcgggg t                               31

<210> SEQ ID NO 37
<211> LENGTH: 31
<212> TYPE: DNA
<213> ORGANISM: Artificial Sequence
<220> FEATURE:
<223> OTHER INFORMATION: Synthetic Construct

<400> SEQUENCE: 37
tttttttttt ttcggagctc gcgagcgggg t                               31

<210> SEQ ID NO 38
<211> LENGTH: 31
<212> TYPE: DNA
<213> ORGANISM: Artificial Sequence
<220> FEATURE:
<223> OTHER INFORMATION: Synthetic Construct

<400> SEQUENCE: 38
tttttttttt ttcggagctc gcaagcgggg t                               31

<210> SEQ ID NO 39
<211> LENGTH: 32
<212> TYPE: DNA
<213> ORGANISM: Artificial Sequence
<220> FEATURE:
<223> OTHER INFORMATION: Synthetic Construct

<400> SEQUENCE: 39
tttttttttt ttaattaaac taagcggaag cc                              32

<210> SEQ ID NO 40
<211> LENGTH: 32
<212> TYPE: DNA
<213> ORGANISM: Artificial Sequence
<220> FEATURE:
<223> OTHER INFORMATION: Synthetic Construct

<400> SEQUENCE: 40
tttttttttt ttaattaaac aaagcggaag cc                              32

<210> SEQ ID NO 41
<211> LENGTH: 31
<212> TYPE: DNA
<213> ORGANISM: Artificial Sequence
<220> FEATURE:
<223> OTHER INFORMATION: Synthetic Construct

<400> SEQUENCE: 41
tttttttttt tttgtcgggc cgcctaggca t                               31

<210> SEQ ID NO 42
<211> LENGTH: 31
<212> TYPE: DNA
<213> ORGANISM: Artificial Sequence
<220> FEATURE:
<223> OTHER INFORMATION: Synthetic Construct

<400> SEQUENCE: 42
tttttttttt tttgtcgggc agcctaggca t                               31

<210> SEQ ID NO 43

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 43
tttttttttt ttcattacca tgagcgctaa cag                                    33

<210> SEQ ID NO 44
<211> LENGTH: 33
<212> TYPE: DNA
<213> ORGANISM: Artificial Sequence
<220> FEATURE:
<223> OTHER INFORMATION: Synthetic Construct

<400> SEQUENCE: 44
tttttttttt ttcattacca tgggcgctaa cag                                    33

<210> SEQ ID NO 45
<211> LENGTH: 31
<212> TYPE: DNA
<213> ORGANISM: Artificial Sequence
<220> FEATURE:
<223> OTHER INFORMATION: Synthetic Construct

<400> SEQUENCE: 45
tttttttttt ttgacgcccg cgaccccact a                                      31

<210> SEQ ID NO 46
<211> LENGTH: 31
<212> TYPE: DNA
<213> ORGANISM: Artificial Sequence
<220> FEATURE:
<223> OTHER INFORMATION: Synthetic Construct

<400> SEQUENCE: 46
tttttttttt ttgacgcccg cgcccccact a                                      31

<210> SEQ ID NO 47
<211> LENGTH: 31
<212> TYPE: DNA
<213> ORGANISM: Artificial Sequence
<220> FEATURE:
<223> OTHER INFORMATION: Synthetic Construct

<400> SEQUENCE: 47
tttttttttt ttgacgcccg caaccccact a                                      31

<210> SEQ ID NO 48
<211> LENGTH: 31
<212> TYPE: DNA
<213> ORGANISM: Artificial Sequence
<220> FEATURE:
<223> OTHER INFORMATION: Synthetic Construct

<400> SEQUENCE: 48
tttttttttt ttgacgcccg cggccccact a                                      31

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct

<400> SEQUENCE: 49
```

```
tcacttgctt ccgttgagg                                            19

<210> SEQ ID NO 50
<211> LENGTH: 32
<212> TYPE: DNA
<213> ORGANISM: Artificial Sequence
<220> FEATURE:
<223> OTHER INFORMATION: Synthetic Construct

<400> SEQUENCE: 50
tttttttttt ttcctcaacg gaagcaagtg at                             32

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
atcacttgct tccgttgagg                                           20

<210> SEQ ID NO 52
<211> LENGTH: 23
<212> TYPE: DNA
<213> ORGANISM: Artificial Sequence
<220> FEATURE:
<223> OTHER INFORMATION: Synthetic Construct

<400> SEQUENCE: 52
tttttttttt ttcaagcagc cac                                       23
```

METHODS, MICROARRAY, AND KITS FOR DETECTION OF DRUG RESISTANCE GENES IN GRAM-NEGATIVE BACTERIA

CROSS-REFERENCE TO RELATED APPLICATIONS

This application is a National Phase filing under 35 U.S.C. §371 of International Application No. PCT/CN2007/000199 having an international filing date of Jan. 18, 2007, which claims priority to Chinese Patent Application No. 200610001309.8, filed on Jan. 18, 2006, the entire content of each of which is incorporated herein by reference.

TECHNICAL FIELD

The present invention relates to methods for detecting drug resistance genes in gram-negative bacteria and microarrays and diagnostic kits thereof.

BACKGROUND

With the intensive use of antimicrobial agents, drug resistance of pathogens to antimicrobial agents is increasing, and the therapy for infection due to resistant bacteria becomes a global problem. The pathogens that cause the clinical bacterial infection include aerobes and anaerobe, and are classified as gram-positive and gram-negative bacteria. Each class includes coccus and rod. Aerobic gram-positive coccus and gram-negative rod are two kinds of the most frequently encountered pathogens. Due to the difference of cell wall and other structures between gram-positive and gram-negative bacteria, the mechanism of drug action and drug resistance displays the significant difference, and the clinical therapy to the two kinds of bacteria are also very different.

Antibiotics are the most frequently used antimicrobial agents. They play an important role in controlling, preventing and treating the infectious diseases. However, since antibiotics were introduced in 1939, especially in recent 10 years, the drug resistance of bacteria is increasing rapidly, and the nosocomial infection is more and more serious.

The emergence of all kinds of different resistant bacteria can cause a serious problem. For example, it can result in the therapy failure, the increase of the complicating disease, the infection recrudescence, the delay of the hospital time, and the increase use of expensive antibiotics and other drugs. The global spread of resistant bacteria is increasing with the development of international trade. Studying of the emergence of resistant bacteria and its occurrence mechanism, and understanding and using the correct detection methods are the key points to in time detect the resistant strains, and to efficiently prevent and control the spread of the resistant strains. Timely and accurate detection of resistant bacteria is important to the rational use of antimicrobials and the development of new antimicrobial agents.

The resistance mechanism of gram-negative bacteria is very complex, including four kinds of major resistance mechanisms. The multi-drug resistance also occurs due to the synergetic effect of different resistance mechanisms.

The Modification or Hydrolysis of Enzymes to Antibiotics

β-lactamase, inactivating the antibiotics by hydrolyzing β-lactam ring, is the most important mechanism for most bacteria to resist β-lactamase, and is the resistance mechanism of about 80% resistant bacteria. More than 200 kinds of β-lactamases have been found. β-lactamase can hydrolyze the β-lactam four-member ring of penicillins, cephalosporins, carbapenems (imipenem and meropenem) and monobactams (aztreonam).

Outer Membrane Impermeability

The membrane porin of gram-negative bacteria is narrow, and can form the effective natural barrier to the macromolecules and hydrophobic compounds. The loss of membrane porin is a major cause of the decrease of membrane impermeability that causes bacterial drug resistance, for example, the loss of OprD2 membrane porin results in the resistance against imipenem in *Pseudomonas aeruginosa* (Huang H, Jeanteur D, Pattus F, Hancock R E. 1995. Membrane topology and site-specific mutagenesis of *Pseudomonas aeruginosa* porin OprD. Mol. Microbiol. 16(5):931-41.) and *Klebsiella pneumoniae* (Martinez-Martinez L, Pascual A, Hernandez-Alles S, Alvarez-Diaz D, Suarez A I, Tran J, Benedi V J, Jacoby G A. 1999. Roles of beta-lactamases and porins in activities of carbapenems and cephalosporins against *Klebsiella pneumoniae*. Antimicrob Agents Chemother. 43(7):1669-73).

Active Efflux Pumps

Active efflux is now known to play a major role in the resistance of many species to antibacterial agents, effluxing many different antibiotics by the synergism of several membrane proteins, and resulting in bacterial multi-drug resistance. Four active efflux pumps are detected in *Pseudomonas aeruginosa* responsible for multiple drug resistance [Masuda N, Sakagawa E, Ohya S. 1995. Outer membrane proteins responsible for multiple drug resistance in *Pseudomonas aeruginosa*. Antimicrob Agents Chemother. 39(3):645-9.]. Among them, only mexAB-oprM is constitutively expressed, and is the basis of multidrug resistance in *P. aeruginosa*.

Alteration of the Antibiotic Target

β-lactam antibiotics bind specifically with PBPs on the cell membrane, and kill bacteria by inhibiting the synthesis of peptidoglycan. The antibiotics loose their functions due to the alteration of PBPs or production of new functional PBPs, resulting in the drug resistance. Since the β-lactamases and outer membrane impermeability play an important role in gram-negative bacteria, the function of PBPs in drug resistance is not significant in gram-negative bacteria.

β-Lactamases

β-lactamases (E.C.3.5.2.6) are the enzymes that can hydrolyze specifically β-lactam ring, and are the leading cause of resistance to β-lactam antibiotics among gram-negative bacteria, accounting 80% in all the resistance mechanisms. β-lactamses are a protein family consisting of many kinds of enzymes. The genes of these proteins exist on the bacterial chromosome or plasmids. The penicillinase that can hydrolyze penicillin was reported followed the use of penicillin nearly at the same time [Abraham E P, Chain E. 1940. An enzyme from bacteria able to destroy penicillin. Nature. 146: 837]. Currently the remarkable problem in gram-negative bacteria is the resistance to the third generation cephalosporin and the new extended-spectrum beta-lactam antibiotics. The major mechanism is the production of extended-spectrum beta lactamases (ESBLs) and Bush group of β-lactamases in bacteria. The active site of penicillinase and AmpC lactamase contains a serine, which attack the carboxyl group of β-lactam as the nucleophilic agent, forms the acyl-enzyme intermediate, then β-lactam ring is destroyed and inactive by the action of water molecules. The active site of mental β-lactamase is bivant Zn atom.

So far more than 200 kinds of different β-lactamases have been reported. They are different in the origin, hydrolytic spectrum, susceptibility to inhibitors and the structures, thus resulting in the difficulty for the systermatic classification.

Seven classification schemes have been proposed. Among them, the functional classification scheme of β-lactamases proposed by Bush, Jacoby and Medeiros [Bush, K., G. A. Jacoby, and A. A. Medeiros. 1995. A functional classification scheme for β-lactamases and its correlation with molecular structure. Antimicrob. Agents Chemother. 39:1211-1233.] is more practical and perfect, which defines the following four groups according to their substrate and inhibitor profiles.

Group 1 cephalosporinases belong to class C enzyme and are not well inhibited by clavulanic acid. These enzymes can hydrolyze preferably cephalosporin and hydrolyze penicillin weakly. Group 1 enzymes are encoded by ampC genes located on the chromosome, and are called AmpC beta-lactamase. The characteristic of the recently found plasmid-mediated AmpC is same as the chromosomal AmpC enzymes, therefore are classified as group 1 enzymes.

Group 2 penicillinases, cephalosporinases, and broad-spectrum β-lactamases belong to class A or D enzymes that hydrolyze mostly penicillin and are generally inhibited by active site-directed β-lactamase inhibitors (except 2br subclass). In addition, extended-spectrum beta lactamases (ESBLs) belong to 2be subclass and can hydrolyze the third generation of cephalosporin.

Group 3 metallo-β-lactamases, also called carbapenemases, belong to class B, including IMP- and VIM-type β-lactamases. Metallo-β-lactamases are located on the chromosome or the plasmids. Their active site contains two Zn atoms, and can hydrolyze almost all β-lactams, and they are poorly inhibited by inhibitor clavulanic acid. However they can be inhibited by EDTA and p-chloromercuribenzoate (pCMB).

Group 4 penicillinases can hydrolyze penicillin and are not well inhibited by clavulanic acid.

The most important β-lactamases in the clinic are extended-spectrum beta lactamases (ESBLs) and cephalosporinase (AmpC).

The Methods for Detection of ESBLs and AmpC

Disc diffusion method: At least two kinds of discs containing cefpodoxime, ceftazidime, aztreonam, cefotaxime or ceftriaxome are used in the initial screening test. Mueller-Hinton agar with discs is inoculated. After incubation, the inhibition zone diameter is measured and the susceptibility is estimated according to Clinical and Laboratory Standards Institute (CLSI) guideline. The CLSI phenotypic confirmatory method for ESBL production uses the discs containing 30 μg of cefotaxime and ceftazidime alone and in combination with 10 μg of clavulanate. Mueller-Hinton agar is inoculated, and discs containing the standard 30 μg of ceftazidime, or cefotaxime are placed 15 mm from the ceftazidime or cefotaxime disc with 10 μg of clavulanic acid. After incubation, an enhanced zone of inhibition ($\geq$5 mm) between any one of the β-lactam discs and the clavulanic acid disc is interpreted as presumptive evidence for the presence of an ESBL. The sensitivity of the method is 84.4%.

Double disc synergy test: A disc containing enzyme inhibitor (such as amoxicillin-clavulanate) is placed in proximity to a disc containing the third generation of cephalosporin (such as ceftazidime, cefotaxime or ceftriaxome) or aztreonam. The clavulanate in the amoxicillin-clavulanate disc diffuses through the agar and inhibits the β-lactamase surrounding the ceftazidime disc. Enhancement of the zone of the ceftazidime disc on the side facing the amoxicillin-clavulanate disc is interpreted as the presence of an ESBL. The sensitivity of the method is about 79%.

Determination of minimum inhibition concentration (MIC): At least two kinds of antibiotics including cefpodoxime, ceftazidime, aztreonam, cefotaxime or ceftriaxome are used in the initial screening test. MH broth is diluted (standard broth dilution method), and the isolate with the MIC of ceftazidime, cefotaxime or ceftriaxome or aztreonam more than 2 mg/ml is considered as the ESBL-producing isolate. The confirmatory test is performed according to the CLSI guideline. MH broths with cefotaxime (or ceftazidime) alone and with cefotaxime (or ceftazidime) plus clavulanate (with a fixed concentration of 4 mg/L) are diluted respectively. The difference of the MIC of cefotaxime (or ceftazidime) alone and with clavulanate more than 8 folds is interpreted as presumptive evidence for the presence of an ESBL.

Etest: Etest ESBLs strip contains ceftazidime on one end, ceftazidime plus clavulanate on another end, and the antibiotic concentrations on the ends are highest, decreasing successively toward the middle. MH agar with E-test strip is inoculated and cultured for 18-24 hours, then measure the MIC on the inhibition lines. The difference of the MIC of ceftazidime alone and with clavulanate more than 4 folds is interpreted as presumptive evidence for the presence of an ESBL. This method is easy-operated and simple, but the cost of the strips is very expensive.

Three dimensional test: Lawn cultures of the susceptible isolate such as *E. coli* ATCC 25922 are prepared on Mueller-Hinton agar plates and cefoxitin 30 μg discs are placed on the plate. Linear slits are cut using a sterile surgical blade 3 mm away from the cefoxitin disc and the isolate culture or the extract is loaded. The plates are kept upright for 5-10 min until the solution dried, and are then incubated at 37° C. overnight. The disturbance of the inhibition zone of the susceptible strain by the tested culture or the extract is interpreted as positive. The sensitivity of this method is 95%. However, the method is labor-intensive, and the expert is needed for operation.

The above phenotypic detection method (except three dimensional test) only can be used to detect *E. coli, K. pneumoniae* and *K. oxytoca*, and can not be used for other Enterobacteriaceae, also can not be used to detect AmpC enzymes. Three dimensional test can detect AmpC enzymes, but it is difficult to perform in the clinical laboratory.

Besides the said phenotypic resistance detection methods, some molecular methods can also be used to detect ESBLs, such as detection of pI of ESBLs (isoelectric focusing, IEF), analysis of the hydrolytic spectrum of enzyme for typing or PCR amplification. The advantages of the molecular methods are rapidness and accuracy. When the MIC is the critical value, molecular methods can provide useful information for clinical therapy. However, the detection target of the traditional molecular method is few, thus the practical application is not good.

The disclosures of all publications, patents, patent applications and published patent applications referred to herein are hereby incorporated herein by reference in their entirety.

BRIEF SUMMARY OF THE INVENTION

The present invention provides methods, kits, and microarrays for detection of drug resistance genes in gram-negative bacteria.

In one aspect, there is provided a kit for detecting one or more drug resistance genes in gram-negative bacteria, comprising: a) one or more primer pairs for amplification of a drug resistance gene; and/or b) one or probes for detection of at least one drug resistance gene. In some embodiments, the kit comprises one or more primer pairs for amplification of a drug resistance gene. In some embodiments, the kit comprises one or probes for detection of at least one drug resistance gene. In some embodiments, the kit comprises: a) one or more primer pairs for amplification of a drug resistance gene; and b) one or probes for detection of at least one drug resistance gene.

In some embodiments, the gram-negative bacteria is selected from the group consisting of *E. coli, K. pneumoniae*, and *E. cloacae*. In some embodiments, the drug resistance gene is selected from the group consisting of tem, shv, ctx-m-1-type, ctx-m-9-type, mox, cit, dha, acc, ebc, and fox.

In some embodiments, the kit comprises primer pairs for amplification of at least two drug resistance genes. In some embodiments, the kit comprises primer pairs for amplification of at least five drug resistance genes. In some embodiments, the kit comprises at least any of 1, 2, 3, 4, 5, 6, 7, 8, 9, or 10 primer pairs listed on Table 1, or homologues thereof. In some embodiments, at least one primer of the primer pairs is linked to a universal tagged sequence, such as a universal tagged sequence labeled with a marker (such as fluorescent marker such as Cy3, Cy5 or TAMRA). In some embodiments, the universal tagged sequence has the nucleotide sequence of SEQ ID NO:1.

In some embodiments, the kit comprises one or more probes (such as probes having about 15-35 nucleotides) for detecting at least one drug resistance gene. In some embodiments, the kit comprises at least any of 1, 2, 3, 4, 5, 10, 15, 20, or 21 probes listed in Table 2, or homologues thereof. In some embodiments, the 5' end of the probe is linked with a poly (dT) of about 10-35 nucleotides (such as about 12-18 nucleotides). In some embodiments, the probe detects at least one drug resistance gene selected from the group consisting of tem, shv, ctx-m-1-type, ctx-m-9-type, mox, cit, dha, acc, ebc, and fox.

The probes in the kit may be immobilized on a carrier (such as a microarray, a glass slide or a nylon membrane). For example, in some embodiments, there is provided a microarray for detection of a drug resistance gene in gram-negative bacteria, comprising at least one probe for a drug resistance gene. In some embodiments, the microarray comprises a probe for detecting tem (such as universal tem probe having the nucleotide sequence of SEQ ID NO:22 or homologues thereof), shv (such as universal shv probe having the nucleotide sequence of SEQ ID NO:33 or homologues thereof and specific shv probe having the nucleotide sequence of SEQ ID NO: 34-48 or a homologue thereof), ctx-m-1-type (such as universal ctx-m-1-type probe having the nucleotide sequence of SEQ ID NO:24 or homologues thereof), ctx-m-9-type (such as universal ctx-m-9-type probe having the nucleotide sequence of SEQ ID NO:23 or homologues thereof), mox (such as universal mox probe having the nucleotide sequence of SEQ ID NO:25 or homologues thereof), cit (such as universal cit probe having the nucleotide sequence of SEQ ID NO:26 or homologues thereof), dha (such as universal dha probe having the nucleotide sequence of SEQ ID NO:27 or homologues thereof), acc (such as universal acc probe having the nucleotide sequence of SEQ ID NO:28 or homologues thereof), ebc (such as universal ebc probe having the nucleotide sequence of SEQ ID NOs 29-31 or homologues thereof), and fox (such as universal fox probe having the nucleotide sequence of SEQ ID NO:32 or homologues thereof).

In some embodiments, at least one of the drug resistance genes is tem and at least one primer pair comprises nucleotides having the sequences of SEQ ID NO:2 and SEQ ID NO:3, or homologues thereof. In some embodiments, the kit further comprises a tem universal probe.

In some embodiments, at least one of the drug resistance genes is shv and at least one pair of the primers are nucleotides having the sequences of SEQ ID NO:4 and SEQ ID NO:5, or homologues thereof. In some embodiments, the kit further comprises a shv universal probe. In some embodiments, the kit further comprises a shv typing probe.

In some embodiments, at least one of the drug resistance genes is ctx-m-1-type and at least one pair of the primers are nucleotides having the sequences of SEQ ID NO: 6 and SEQ ID NO:7, or homologues thereof. In some embodiments, the kit further comprises a ctx-m-1-type universal probe.

In some embodiments, at least one of the drug resistance genes is ctx-m-9-type and at least one pair of the primers are nucleotides having the sequences of SEQ ID NO:8 and SEQ ID NO:9, or homologues thereof. In some embodiments, the kit further comprises a ctx-m-9-type universal probe.

In some embodiments, at least one of the drug resistance genes is mox and at least one pair of the primers are nucleotides having the sequences of SEQ ID NO:10 and SEQ ID NO: 11, or homologues thereof. In some embodiments, the kit further comprises a mox universal probe.

In some embodiments, at least one of the drug resistance genes is cit and at least one pair of the primers are nucleotides having the sequences of SEQ ID NO: 12 and SEQ ID NO: 13, or homologues thereof. In some embodiments, the kit further comprises a cit universal probe.

In some embodiments, at least one of the drug resistance genes is dha and at least one pair of the primers are nucleotides having the sequences of SEQ ID NO:14 and SEQ ID NO: 15, or homologues thereof. In some embodiments, the kit further comprises a dha universal probe.

In some embodiments, at least one of the drug resistance genes is acc and at least one pair of the primers are nucleotides having the sequences of SEQ ID NO:16 and SEQ ID NO:17, or homologues thereof. In some embodiments, the kit further comprises an acc universal probe.

In some embodiments, at least one of the drug resistance genes is ebc and at least one pair of the primers are nucleotides having the sequences of SEQ ID NO:18 and SEQ ID NO:19, or homologues thereof. In some embodiments, the kit further comprises an ebc universal probe.

In some embodiments, at least one of the drug resistance genes is fox and at least one pair of the primers are nucleotides having the sequences of SEQ ID NO:20 and SEQ ID NO:21, or homologues thereof. In some embodiments, the kit further comprises a fox universal probe.

The kits or microarrays described above may further comprise one or more control probes, for example control probes selected from the group consisting of: surface chemistry control probe (such as a probe having the nucleotide sequence of SEQ ID NO:49, or a homologue thereof), hybridization control probe (such as a probe having the nucleotide sequence of SEQ ID NO:50, or a homologue thereof), and negative control probe (such as a probe having the nucleotide sequence of SEQ ID NO:52, or a homologue thereof). In some embodiments, the kit further comprises a target for hybridization control (such as a probe having the nucleotide sequence of SEQ ID NO:51, or a homologue thereof). In some embodiments, the kit comprises solutions for PCR reaction and/or solutions for hybridization reaction.

In another aspect, there are provided methods of detecting a drug resistance gene in gram-negative bacteria using kits or microarrays described herein. In some embodiments, there is provided a method for detecting a drug resistance gene in gram-negative bacteria comprising: a) performing PCR using at least one primer pair that amplify a drug resistance gene of gram-negative bacteria; and b) hybridizing the amplified products with one or more probes there detect a drug resistance gene. In some embodiments, the drug resistance gene is selected from the group consisting of tem, shv, ctx-m-1-type, ctx-m-9-type, mox, cit, dha, acc, ebc, and fox. In some embodiments, the PCR is multiplex asymmetric PCR. In some embodiments, the concentrations of the two primers in each pair are equal. In some embodiments, one of the primers in each pair is tagged with a universal tagged sequence at the 5' end, and wherein the concentration of the primer with the universal tagged sequence is 5-100 folds of that of the untagged primer. In some embodiments, the PCR comprises 10-25 cycles of denaturation, annealing, and extension, followed by 10-25 cycles of denaturation.

DETAILED DESCRIPTION OF THE INVENTION

Figure 1:
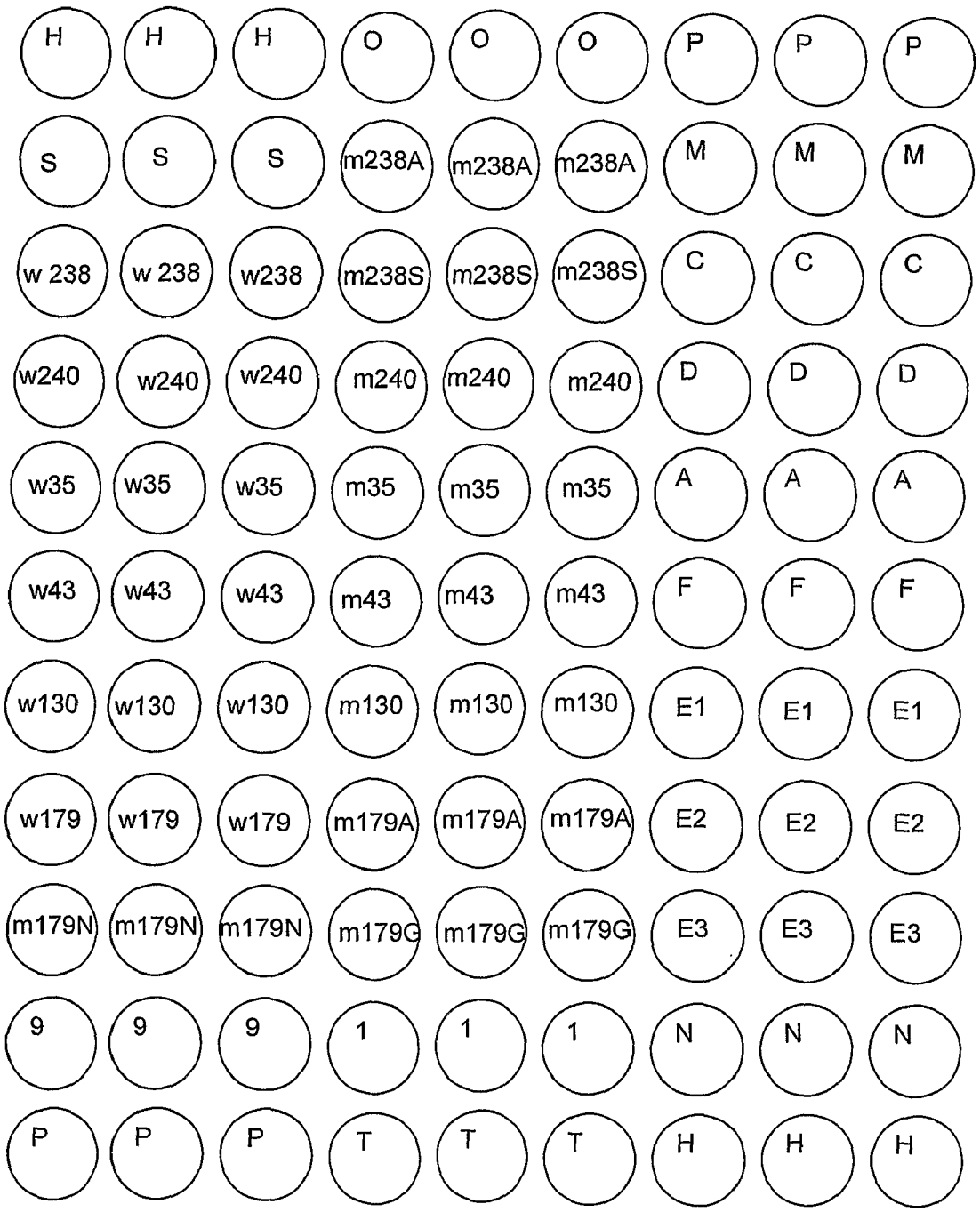
FIG. 1 provides a schematic diagram of an exemplary array of probes.

The present invention provides primers and probes for detecting drug resistance genes in gram-negative bacteria. The primers are capable of amplifying one or more drug resistance genes, and the probes are capable of detecting the drug resistance genes and amplification products of the drug resistance genes.

In one aspect, there are provided kits for detecting drug resistance genes in gram-negative bacteria. In some embodiments, the kit comprises one or more primer pairs for amplification of a drug resistance gene. In some embodiments, the kit comprises one or probes for detection of at least one drug resistance gene. In some embodiments, the kit comprises: a) one or more primer pairs for amplification of a drug resistance gene; and b) one or probes for detection of at least one drug resistance gene. The probes may be immobilized in a carrier, for example, in the form of microarrays.

Also provided are methods of detecting drug resistant genes in gram-negative bacteria using kits and microarrays described herein.

"Homologues" of drug resistance genes, primers, and sequences as used herein refers to nucleotide sequences having at least about 40%, including for example at least about any of 50%, 60%, 70%, 80%, 90%, 95%, 98%, 99%, or more sequence identity to the sequence of nucleotide sequences of genes, primers, or probes described herein.

Drug Resistance Genes in Gram-Negative Bacteria

Gram-negative bacteria are known in the art, and can be identified by methods such as gram stain. Suitable gram-negative bacteria include, but are not limited to, *E. coli, K. pneumoniae, K. oxytoca, E. cloacae, Enterobacter aerogenes, Citrobacter freundii, Pseudomonas aeruginosa, Acinetobacter calcoaceticus, Acinetobacter calcoaceticus,* and *Hemophilus influenzae*. Gram stain is a very simple and rapid conventional detection method in the clinic. The present invention is applicable to the most prevalent gram-negative bacteria and the most important resistance genes thereof, thus having the significant clinical applications. The detection time is greatly shortened and the clinical application is increased in the present invention, so that the present invention is important to rational use of antimicrobials, individual therapy, and control of the spread of the resistant strains.

Drug resistance genes in gram-negative bacteria include, but are not limited to, penicilinases such as TEM-1, TEM-2, SHV-1, cephalosporinases such as DHA-1, MIR-1, ACT-1, CMY-2, extended-spectrum β-lactamase such as TEM-3, CMY-2, SHV-2, SHV-12, penicillinases such as PSE-1, PSE-3, OXA-1.

In some embodiments, the drug resistance gene is an extended-spectrum β-lactamase gene. Extended-spectrum β-lactamases (ESBLs) are the plasmid-mediated enzymes that can confer resistance to multiple β-lactam antibiotics. ESBLs are produced by gram-negative bacteria, especially *E. coli* and *K. pneumoniae*, belonging to 2be subclass of BJM functional classification scheme. They are constitutively expressed, and hydrolyze extended-spectrum cephalosporins such as cefotaxime and ceftazidime, monobactams such as aztreonam, but can be inhibited by clavulanate and sulbactam. Most ESBLs are the derivatives of broad-spectrum β-lactamases TEM-1, TEM-2 and SHV-1 by mutations, and the hydrolytic spectrum is enlarged, so that ESBLs can hydrolyze many oxyimino β-lactam antibiotics.

Currently more than 200 kinds of ESBLs, including 144 TEM-type ESBLs, 52 SHV-type ESBLs, 14 OXA-type ESBLs, 24 CTX-M-type ESBLs and ten of other ESBLs, have been reported.

CTX-M-type ESBLs are the most prevalent ESBLs in China. Wang H, Kelkar S, Wu W, Chen M, Quinn J P. 2003, 47(2):790-3. Among them, CTX-M-11, 13, 14 and 15 were detected in Beijing and Guangzhou. Some other ESBLs are SHV-type ESBLs, and no TEM-type ESBLs are detected in China. This phenomenon may be related to the extensive use of cefotaxime in China, therefore selecting CTX-M-type ESBLs that are cefotaxime-resistant and ceftazidime-susceptible.

In some embodiments, the drug resistance gene is a cephalosporinase gene. Cephalosporinases (AmpC enzymes) have the homology in molecular structure and belong to molecular class C enzymes. AmpC enzymes exist in most of Enterobacteriaceae and *Pseudomonas aeruginosa*, and are located on the chromosome or plasmids. Originally AmpC enzymes are mediated by chromosome, produced naturally, and most exist in *Enterobacter cloacae, Citrobacter freundii, Serratia marcescens* and *Pseudomonas aeruginosa*. Recently AmpC begins to transfer into the plasmids. Most of plasmid-mediated AmpC have no regulation genes, thus constitutively expressed (except DHA-1). Due to the rapid replication of the plasmid (resulting in the increase of mutation) and the transferable property (resulting in the rapid spread), plasmid-mediated AmpC enzyme can select more clinical resistant strains. The first plasmid-mediated AmpC enzyme CMY-1 that is resistant to cefoxitin and cefotetan was reported in 1989, with a pI 8.0. This enzyme can transfer the drug resistance from *K. pneumoniae* into *E. coli*. Bauernfeind et al., 1989, Infection 17:316-321. Since then, more and more plasmid-mediated AmpC enzymes are found and reported. They can confer the resistance to oxyimino- and 7α-methoxy-cephalosporins. The plasmids harboring these enzymes are transferable. Plasmid-mediated AmpC enzymes distribute mainly in *K. pneumoniae* and other Enterobacteriaceae. The increase of new enzymes is 1-2 every year. This is a new danger, and should pay a significant attention.

In total, 33 kinds of plasmid-mediated AmpC enzymes have been found. They can be classified as six groups according to the homology to chromosomal AmpC enzymes (Philippon et al. 2002, Antimicrob Agents Chemother. 46(1):1-11) including MOX-CMY group; CMY-LAT group (also called CIT group due to the origin from *Citrobacter* AmpC); DHA group, ACC group, EBC group and FOX group. Among them, cmy-2 in CIT group is the most prevalent plasmid-mediated ampC gene in the world, found in Asia, America and Europe. Philippon et al., 2002, Antimicrob Agents Chemother. 46(1): 1-11. The hydrolytic spectrum of plasmid-mediated AmpC enzyme is broad. They can hydrolyze oxyimino- (such as the third generation of cephalosporin) and 7α-methoxy- (such as cefoxitin) antibiotics, also they are not inhibited by enzyme inhibitor clavulanate as the chromosomal AmpC enzymes. In addition, plasmid-mediated AmpC enzymes can cause the resistance to carbapenems by the combination with the loss of specific porins. For example, the synergism of plasmid-mediated CMY-4 and the loss of porins can cause the resistance to imipenem in *K. pneumoniae* (Cao et al., 2000, J Antimicrob Chemother. 46(6):895-900), which is a problem in the clinical therapy.

In some embodiments, the drug resistance gene is selected from the group consisting of tem, shv, ctx-m-1-type, ctx-m-9-type, mox, cit, dha, acc, ebc, and fox.

The term "tem" refers to a TEM-type ESBL gene, which includes, but is not limited to, tem-1 to ten 144, or their homologues.

The term "shv" refers to a SHV-type ESBL gene, which includes, but is not limited to, shv-1 to shv-16, shv-2a, shv-18 to shv-22, shv-24 to shv-46, shv-48 to shv-51, shv-53, shv-57, shv-59, shv-70 and homologues thereof.

The term the "ctx-m-1-type" refers to a CTX-M-1-type ESBL gene, which includes, but is not limited to, ctx-m-1, ctx-m-3, ctx-m-10, ctx-m-12, ctx-m-15 and fec-1.

The term "ctx-m-9-type" refers to a CTX-M-9-type ESBL gene, which includes but is not limited to, ctx-m-9, ctx-m-13, ctx-m-14, ctx-m-16, ctx-m-17, ctx-m-19, ctx-m-21, ctx-m-27 and Toho-2.

The term "mox" refers to a MOX group of cephalosporinase gene, which includes, but is not limited to, cmy-1, cmy-8 to cmy-11, mox-1 and mox-2.

The term "cit" refers to a CIT group of cephalosporinase gene, which includes, but is not limited to, cmy-2, bil-1, cmy-2b, cmy-4 to cmy-7, cmy-12, lat-1 to lat-4.

The term "dha" refers to a DHA group of cephalosporinase gene, which includes, but is not limited to, dha-1 and dha-2.

The term "acc" refers to an ACC group of cephalosporinase gene, which includes, but is not limited to, aac-1.

The term "ebc" refers to an EBC group of cephalosporinase gene, which includes, but is not limited to, mir-1, act-1 and *E. cloacae* chromosomal ampC gene.

The term "fox" refers to a FOX group of cephalosporinase gene, which include, but is not limited to, fox-1 to fox-6.

Primers for Amplification of Drug Resistance Genes

The present invention provides kits comprising primers for amplifying drug resistance genes. For example, the primers may comprise forward and reverse primers for amplifying drug resistance genes by PCR methods, such as asymmetric PCR methods.

The forward and reverse primer of primer pairs described herein for amplification of the drug resistance genes in gram-negative bacteria are typically 10-50 nucleotides, including for example 12-35 nucleotides, 15-25 nucleotides. In some embodiments, the 5'-end of the forward or reverse primer of the said primer pairs for amplification of the drug resistance genes in gram-negative bacteria is linked with a universal tagged sequence. The 5'-end of the said universal tagged sequence in some embodiments may be labeled with a fluorescent dye. Exemplary universal tagged sequence has the nucleotide sequence as set forth in SEQ ID NO: 1.

In some embodiments, the kit comprises at least about two different primer pairs. In some embodiments, the kit comprises at least about three different primer pairs. In some embodiments, the kit comprises at least about any of 3, 4, 5, 6, 7, 8, 9, 10, 20, 30, 40, or 50 different primer pairs. These different primer pairs may amplify the same drug resistance gene, different drug resistance genes, or different regions of the same drug resistance gene. In some embodiments, the kit comprises at least any of 1, 2, 3, 4, 5, 6, 7, 8, 9, 10 pairs of primers listed in Table 1, or homologues thereof.

TABLE 1

The primers in the kit for detection of the resistance genes in gram-negative bacteria in the present invention

| Target gene | Amplicon length (bp) | Primer No. | Primer type | Primer sequence (5'-3') | ID |
|---|---|---|---|---|---|
| / | / | H | 5-universal tagged sequence | TAMRA-GGTTTCGGATGTTACAGCGT | 1 |
| tem | 744 | tem-f | tem forward primer | CGCCCTTATTCCCTTTTTTGCGG | 2 |
|  |  | tem-ur | tem reverse tagged primer | H-TCAGTGAGGCACCTATCTCAGCG | 3 |
| shv | 885 | shv-f | shv forward primer | TCACTCAAGGATGTATTGTTGG | 4 |
|  |  | shv-ur | shv reverse tagged primer | H-TTAGCGTTGCCAGTGCTCG | 5 |
| ctx-m-1-type | 771 | ctx-1-uf | ctx-1 forward primer | H-CCGTCACGCTGTTGTTAGGAAGTG | 6 |
|  |  | ctx-1-r | ctx-1 reverse tagged primer | CCTTAGGTTGAGGCTGGGTGAAGT | 7 |
| ctx-m-9-type | 631 | ctx-9-uf | ctx-9 forward primer | H-TGCAACGGATGATGTTCGCGG | 8 |
|  |  | ctx-9-r | ctx-9 reverse tagged primer | CCTTTGAGCCACGTCACCAAC | 9 |
| mox | 520 | mox-uf | mox forward primer | H-GCTGCTCAAGGAGCACAGGAT | 10 |
|  |  | mox-r | mox reverse tagged primer | CACATTGACATAGGTGTGGTGC | 11 |
| cit | 462 | cit-uf | cit forward primer | H-TGGCCAGAACTGACAGGCAAA | 12 |
|  |  | cit-r | cit reverse tagged primer | TTTCTCCTGAACGTGGCTGGC | 13 |
| dha | 405 | dha-uf | dha forward primer | H-AACTTTCACAGGTGTGCTGGGT | 14 |
|  |  | dha-r | dha reverse tagged primer | CCGTACGCATACTGGCTTTGC | 15 |
| acc | 346 | acc-uf | acc forward primer | H-AACAGCCTCAGCAGCCGGTTA | 16 |
|  |  | acc-r | acc reverse tagged primer | TTCGCCGCAATCATCCCTAGC | 17 |

TABLE 1-continued

The primers in the kit for detection of the resistance genes in gram-negative bacteria in the present invention

| Target gene | Amplicon length (bp) | Primer No. | Primer type | Primer sequence (5'-3') | ID |
|---|---|---|---|---|---|
| ebc | 302 | ebc-uf | ebc forward primer | H-TCGGTAAAGCCGATGTTGCGG | 18 |
|  |  | ebc-r | ebc reverse tagged primer | CTTCCACTGCGGCTGCCAGTT | 19 |
| fox | 190 | fox-uf | fox forward primer | H-AACATGGGGTATCAGGOAGATG | 20 |
|  |  | fox-r | fox reverse tagged primer | CAAAGCGCGTAACCGGATTGG | 21 |

In some embodiments, the kit comprises a primer pair for amplification of tem comprising a forward primer (such as a primer having the nucleotide sequence as set forth in SEQ ID NO: 2) and the reverse primer (such as a primer having the nucleotide sequence as set forth in SEQ ID NO: 3. These primers can amplify tem (such as tem genes described herein).

In some embodiments, the kit comprises a primer pair for amplification of shv comprising a forward primer (such as a primer having the nucleotide sequence as set forth in SEQ ID NO:4), and a reverse primer (such as a primer having the nucleotide sequence as set forth in SEQ ID NO: 5. These primers can amplify shv (such as the shv genes described herein).

In some embodiments, the kit comprises a primer pair for amplification of ctx-m-1-type comprising a forward primer (such as a primer having the nucleotide sequence as set forth in SEQ ID NO:6), and a reverse primer (such as a primer having the nucleotide sequence as set forth in SEQ ID NO:7). These primers can amplify ctx-m-1-type (such as the ctx-m-1-type genes described herein).

In some embodiments, the kit comprises a primer pair for amplification of ctx-m-9-type comprising a forward primer (such as a primer having the nucleotide sequence as set forth in SEQ ID NO:8), and a reverse primer (such as a primer having the nucleotide sequence as set forth in SEQ ID NO:9). These primers can amplify ctx-m-9-type (such as the ctx-m-9-type genes described herein).

In some embodiments, the kit comprises a primer pair for amplification of mox comprising a forward primer (such as a primer having the nucleotide sequence as set forth in SEQ ID NO:10), and a reverse primer (such as a primer having the nucleotide sequence as set forth in SEQ ID NO:11). These primers can amplify mox (such as the mox genes described herein).

In some embodiments, the kit comprises a primer pair for amplification of cit comprising a forward primer (such as a primer having the nucleotide sequence as set forth in SEQ ID NO:12), and a reverse primer (such as a primer having the nucleotide sequence as set forth in SEQ ID NO:13). These primers can amplify cit (such as the cit described herein).

In some embodiments, the kit comprises a primer pair for amplification of dha comprising a forward primer (such as a primer having the nucleotide sequence as set forth in SEQ ID NO:14), and a reverse primer (such as a primer having the nucleotide sequence as set forth in SEQ ID NO:15). These primers can amplify dha (such as the dha genes described herein).

In some embodiments, the kit comprises a primer pair for amplification of acc comprising a forward primer (such as a primer having the nucleotide sequence as set forth in SEQ ID NO:16), and a reverse primer (such as a primer having the nucleotide sequence as set forth in SEQ ID NO:17). These primers can amplify acc (such as the acc genes described herein).

In some embodiments, the kit comprises a primer pair for amplification of ebc comprising a forward primer (such as a primer having the nucleotide sequence as set forth in SEQ ID NO:18), and a reverse primer (such as a primer having the nucleotide sequence as set forth in SEQ ID NO:19). These primers can amplify ebc (such as the ebc genes described herein).

In some embodiments, the kit comprises a primer pair for amplification of fox comprising a forward primer (such as a primer having the nucleotide sequence as set forth in SEQ ID NO:20), and a reverse primer (such as a primer having the nucleotide sequence as set forth in SEQ ID NO:21). These primers can amplify fox (such as the fox genes described herein).

Probes for Detecting Drug Resistance Genes

In some embodiments, the kits comprise probes for detecting drug resistance genes in gram-negative bacteria. These probes are capable of hybridizing with the drug resistance gene products (including DNA or RNA transcribed from the genes) or amplification of the gene products. In some embodiments, the probes are about 15-50 nucleotides long, including for example about 20-30 nucleotides long. In some embodiments, the 5' end of the probes are linked with an oligonucleotide. For example, the 5' end of the probes may be linked with an oligo-dT that is about 10-35 nucleotides, including for example about 12-18 nucleotides.

In some embodiments, the kit comprises at least about two different probes. In some embodiments, the kit comprises at least about three different probes. In some embodiments, the kit comprises at least about any of 3, 4, 5, 6, 7, 8, 9, 10, 20, 30, 40, or 50 different probes. These probes may detect the same or different drug resistance genes. In some embodiments, the kit comprises at least about any of 1, 2, 3, 4, 5, 10, 15, 20, or 21 probes listed in Table 2, or homologues thereof.

TABLE 2

The probes in the kit for detection of the resistance genes
in gram-negative bacteria in the present invention

| Probe no. | Probe type | Probe sequence (5'-3') | ID |
|---|---|---|---|
| pBB-0201027 | Tem universal probe | 5'-NH2-T12-CGACGAGCGTGACACCACG-3' | 22 |
| PBB-0201032 | ctx-m-9-type universal probe | 5'-NH2-T12-GGAATGGCGGTATTCAGCGTA-3' | 23 |
| PBB-0201033 | ctx-m-1-type universal probe | 5'-NH2-T12-TTCGTCTCCCAGCTGTCGG-3' | 24 |
| PBB-0201031 | mox universal probe | 5'-NH2-T12-CGCCTTGTCATCCAGCTGCA-3' | 25 |
| PBB-0201025 | cit universal probe | 5'-NH2-T12-GCTTTATCCCTAACGTCATCGGG-3' | 26 |
| PBB-0401031 | dha universal probe | 5'-NH2-T12-TGTGATCCCCTTCCACT-3' | 27 |
| PBB-0201035 | acc universal probe | 5'-NH2-T12-TACTCAGCGAACCCACTTCA-3' | 28 |
| PBB-0401051 | ebc universal probe | 5'-NH2-T12-AGGGAGGCGTTATCCGT-3' | 29 |
| PBB-0201036 | ebc universal probe | 5'-NH2-T12-TAGAGCCCAGCTCAAACAG-3' | 30 |
| PBB-0201037 | ebc universal probe | 5'-NH2-T12-CAAGGTTTGTGGAGTGACAG-3' | 31 |
| PBB-0201063 | fox universal probe | 5'-NH2-T12-CGGTGTGGGTCAGCGCGATC-3' | 32 |
| PBB-0201006 | shv universal probe | 5'-NH2-T12-GGCTGGTTTATCGCCGATA-3' | 33 |
| PBB-0201012 | shv typing probe, 238 position G, wild | 5'-NH2-T12-CGGAGCTGGCcAGCGGGGT-3' | 34 |
| PBB-0201013 | shv typing probe, 238 position S, mutant | 5'-NH2-T12-CGGAGCTAGCcAGCGGGGT-3' | 35 |
| PBB-0201039 | shv typing probe, 238 position A, mutant | 5'-NH2-T12-CGGAGCTGCCcARCGGGGT-3' | 36 |
| PBB-0201014 | shv typing probe, 240 position E, wild | 5'-NH2-T12-CGGAGCTcGCGAGCGGGGT-3' | |
| PBB-0201015 | shv typing probe, 240 position K, mutant | 5'-NH2-T12-CGGAGCTcGCAAGCGGGGT-3' | 38 |
| PBB-0201016 | shv typing probe, 35 position L, wild | 5'-NH2-T12-AATTAAACTAAGCGgAAGCC-3' | 39 |
| PBB-0201017 | shv typing probe, 35 position Q, mutant | 5'-NH2-T12-AATTAAACAAAGCGgAAGCC-3' | 40 |
| PBB-0201029 | shv typing probe, 43 position R, wild | 5'-NH2-T12-TGTCGGGCCGCcTAGGCAT-3' | 41 |
| PBB-0201030 | shv typing probe, 43 position S, mutant | 5'-NH2-T12-TGTCGGGCAGCcTAGGCAT-3' | 42 |
| pBB-0201044 | shv typing probe, 130 position S, wild | 5'-NH2-T12-CATTACCATGAGCGcTAACAG-3' | 43 |
| pBB-0201045 | shv typing probe, 130 position G, mutant | 5'-NH2-T12-CATTACCATGGGCGcTAACAG-3' | 44 |
| pBB-0201040 | shv typing probe, 179 position D, wild | 5'-NH2-T12-GACGCCCGCGACcCCACTA-3' | 45 |
| pBB-0201041 | shv typing probe, 179 position A, mutant | 5'-NH2-T12-GACGCCCGCGCCcCCACTA-3' | 46 |
| pBB-0201042 | shv typing probe, 179 position N, mutant | 5'-NH2-T12-GACGCCCGCAACcCCACTA-3' | 47 |
| pBB-0201043 | shv typing probe, 179 position G, mutant | 5'-NH2-T12-GACGCCCGCGGCcCCACTA-3' | 48 |
| PBB-0201090 | Surface chemistry control probe | 5'-HEX-TCACTTGCTTCCGTTGAGG-NH2-3' | 49 |
| PBB-0204652 | Hybridization control probe (EC) | 5'-NH2-T12-CCTCAACGGAAGCAAGTGAT-3' | 50 |
| PBB-0204653 | Hybridization control target | 5'-TAMRA-ATCACTTGCTTCCGTTGAGG-3' | 51 |
| PHB-HC10 | Negative control probe | 5'-NH2-T12-CAAGCAGCCAC-3' | 52 |

Note:
R = A or G;
hybridization control target is used to monitor the hybridization process.

Suitable probes described herein include, but are not limited to, tem universal probe, shv universal probe, ctx-m-1-type universal probe, ctx-m-9-type universal probe, mox universal probe, cit universal probe, dha universal probe, acc universal probe, ebc universal probe and fox universal probe, and shv typing probes.

Suitable shv typing probes include, but are not limited to, probe for detection of amino acid 238 G from amino end of SHV-type ESBL, probe for detection of amino acid 238 S from amino end of SHV-type ESBL, probe for detection of amino acid 238 A from amino end of SHV-type ESBL, probe for detection of amino acid 240 E from amino end of SHV-type ESBL, probe for detection of amino acid 240 K from amino end of SHV-type ESBL, probe for detection of amino acid 35 L from amino end of SHV-type ESBL, probe for detection of amino acid 35 Q from amino end of SHV-type ESBL, probe for detection of amino acid 43 R from amino end of SHV-type ESBL, probe for detection of amino acid 43 S from amino end of SHV-type ESBL, probe for detection of amino acid 130 S from amino end of SHV-type ESBL, probe for detection of amino acid 130 G from amino end of SHV-type ESBL, probe for detection of amino acid 179 D from amino end of SHV-type ESBL, probe for detection of amino acid 179 A from amino end of SHV-type ESBL, probe for detection of amino acid 179 N from amino end of SHV-type ESBL, and probe for detection of amino acid 179 G from amino end of SHV-type ESBL.

Suitable tem universal probes include a probe having the nucleotide sequence as set forth in SEQ ID NO: 22, which is capable of detecting the genes of 144 kinds of TEM-type ESBLs (tem-1 to tem-144).

Suitable shv universal probes include a probe having the nucleotide sequence as set forth in SEQ ID NO: 33, which is capable of detecting the genes of 53 kinds of SHV-type ESBLs (shv-1 to shv-16, shv-2a, shv-18 to shv-22, shv-24 to shv-46, shv-48 to shv-51, shv-53, shv-57, shv-59 and shv-70).

Suitable ctx-m-1-type universal probe include a probe having the nucleotide sequence as set forth in SEQ ID NO: 24, which is capable of detecting the genes of 6 kinds of CTX-M-1-type ESBLs, including ctx-m-1, ctx-m-3, ctx-m-10, ctx-m-12, ctx-m-15 and fec-1.

Suitable ctx-m-9-type universal probe include a probe having the nucleotide sequence as set forth in SEQ ID NO: 23, which is capable of detecting the genes of 9 kinds of CTX-M-9-type ESBLs, including ctx-m-9, ctx-m-13, ctx-m-14, ctx-m-16, ctx-m-17, ctx-m-19, ctx-m-21, ctx-m-27 and Toho-2.

Suitable mox universal probe include a probe having the nucleotide sequence as set forth in SEQ ID NO: 25, which is capable of detecting the genes of 7 kinds of MOX group of cephalosporinase genes including cmy-1, cmy-8 to cmy-11, mox-1 and mox-2.

Suitable cit universal probe include a probe having the nucleotide sequence as set forth in SEQ ID NO: 26, which is capable of detecting the genes of 12 kinds of CIT group of cephalosporinase genes including cmy-2, bil-1, cmy-2b, cmy-4 to cmy-7, cmy-12, and lat-1 to lat-4.

Suitable dha universal probe include a probe having the nucleotide sequence as set forth in SEQ ID NO: 27, which is capable of detecting the genes of 2 kinds of DHA group of cephalosporinase genes including dha-1 and dha-2.

Suitable acc universal probe includes a probe having the nucleotide sequence as set forth in SEQ ID NO: 28 in the sequence list, detecting the gene of one kind of ACC group of cephalosporinase gene including acc-1.

Suitable ebc universal probe include a probe having the nucleotide sequence as set forth in SEQ ID NO: 29 or 30 or 31, which is capable of detecting the genes of 3 kinds of EBC group of cephalosporinase genes including mir-1, act-1 and *E. cloacae* chromosomal ampC gene.

Suitable fox universal probes include a probe having the nucleotide sequence as set forth in SEQ ID NO: 32, which is capable of detecting the genes of 6 kinds of FOX group of cephalosporinase genes including fox-1 to fox-6.

Suitable probes for detection of a SHV-type ESBL gene having amino acid 238 G from the amino end include a probe having the nucleotide sequence as set forth in SEQ ID NO: 34, which is capable of detecting the genes of 32 kinds of SHV-type ESBLs with amino acid 238 G from amino end including shv-1, shv-6, shv-8, shv-11, shv-14, shv-16, shv-19, shv-24 to shv-28, shv-31 to shv-33, shv-35 to shv-38, shv-40 to shv-44, shv-48 to shv-51, shv-53, shv-57, shv-59 and shv-70.

Suitable probes for detection of a SHV-type ESBL gene having amino acid 238 S from the amino end include a probe having the nucleotide sequence as set forth in SEQ ID NO: 35, which is capable of detecting the genes of 18 kinds of SHV-type ESBLs with amino acid 238 S from amino end including shv-2 to shv-5, shv-2a, shv-7, shv-9, shv-10, shv-12, shv-15, shv-20 to shv-22, shv-30, shv-34, shv-39, shv-45 and shv-46.

Suitable probes for detection of a SHV-type ESBL gene having amino acid 238 A from the amino end a probe having the nucleotide sequence as set forth in SEQ ID NO: 36, which is capable of detecting the genes of 3 kinds of SHV-type ESBLs with amino acid 238 A from amino end including shv-13, shv-18 and shv-29.

Suitable probes for detection of a SHV-type ESBL gene having amino acid 240 E from the amino end include a probe having the nucleotide sequence as set forth in SEQ ID NO: 37 in the sequence list, which is capable of detecting the genes of 41 kinds of SHV-type ESBLs with amino acid 240 E from amino end including shv-1 to shv-3, shv-6, shv-8, shv-11, shv-13 to shv-14, shv-16, shv-2a, shv-19 to shv-21, shv-24 to shv-30, shv-32 to shv-44, shv-48 to shv-51, shv-53, shv-57, shv-59 and shv-70.

Suitable probes for detection of a SHV-type ESBL gene having amino acid 240 K from the amino end include a probe having the nucleotide sequence as set forth in SEQ ID NO: 38 in the sequence list, which is capable of detecting the genes of 12 kinds of SHV-type ESBLs with amino acid 240 K from amino end including shv-4, shv-5, shv-7, shv-9, shv-10, shv-12, shv-15, shv-18, shv-22, shv-31, shv-45 and shv-46.

Suitable probes for detection of a SHV-type ESBL gene having amino acid 35 L from the amino end include a probe for the nucleotide sequence as set forth in SEQ ID NO: 39 in the sequence list, which is capable of detecting the genes of 39 kinds of SHV-type ESBLs with amino acid 35 L from amino end including shv-1 to shv-10, shv-14, shv-16, shv-18 to shv-22, shv-24, shv-26 to shv-28, shv-30, shv-32, shv-33 to shv-34, shv-38 to shv-39, shv-41 to shv-46, shv-48 to shv-51, shv-57 and shv-59.

Suitable probes for detection of a SHV-type ESBL gene having amino acid 35 Q from the amino end include a probe having the nucleotide sequence as set forth in SEQ ID NO: 40 in the sequence list, which is capable of detecting the genes of 14 kinds of SHV-type ESBLs with amino acid 35 Q from amino end including shv-2a, shv-11 to shv-13, shv-15, shv-25, shv-29, shv-31, shv-35 to shv-37, shv-40, shv-53 and shv-70.

Suitable probes for detection of a SHV-type ESBL gene having amino acid 43 R from the amino end include a probe for the nucleotide sequence as set forth in SEQ ID NO: 41 in the sequence list, which is capable of detecting the genes of 47 kinds of SHV-type ESBLs with amino acid 43 R from amino end including shv-1 to shv-6, shv-8 to shv-13, shv-15 to shv-16, shv-2a, shv-19 to shv-22, shv-24 to shv-28, shv-31 to shv-33, shv-35 to shv-46, shv-48 to shv-51, shv-53, shv-57, shv-59 and shv-70.

Suitable probes for detection of a SHV-type ESBL gene having amino acid 43 S from the amino end include a probe having the nucleotide sequence as set forth in SEQ ID NO: 42 in the sequence list, which is capable of detecting the genes of 6 kinds of SHV-type ESBLs with amino acid 43 S from amino end including shv-7, shv-14, shv-18, shv-29, shv-30 and shv-34.

Suitable probes for detection of a SHV-type ESBL gene having amino acid 130 S from the amino end include a probe having the nucleotide sequence as set forth in SEQ ID NO: 43 in the sequence list, which is capable of detecting the genes of 52 kinds of SHV-type ESBLs with amino acid 130 S from amino end including shv-1 to shv-9, shv-11 to shv-16, shv-2a, shv-18 to shv-22, shv-24 to shv-46, shv-48 to shv-51, shv-53, shv-57, shv-59 and shv-70.

Suitable probes for detection of a SHV-type ESBL gene having amino acid 130 G from the amino end include a probe having the nucleotide sequence as set forth in SEQ ID NO: 44 in the sequence list, which is capable of detecting the genes of 1 kind of SHV-type ESBL with amino acid 130 G from amino end including shv-10.

Suitable probes for detection of a SHV-type ESBL gene having amino acid 179 D from the amino end include a probe having the nucleotide sequence as set forth in SEQ ID NO: 45 in the sequence list, which is capable of detecting the genes of 50 kinds of SHV-type ESBLs with amino acid 179 D from amino end including shv-1 to shv-5, shv-7, shv-9 to shv-16, shv-2a, shv-18 to shv-22, shv-25 to shv-46, shv-48 to shv-51, shv-53, shv-57, shv-59 and shv-70.

Suitable probes for detection of a SHV-type ESBL gene having amino acid 179 A from the amino end include a probe having the nucleotide sequence as set forth in SEQ ID NO: 46 in the sequence list, which is capable of detecting the genes of 1 kind of SHV-type ESBL with amino acid 179 A from amino end including shv-6.

Suitable probes for detection of a SHV-type ESBL gene having amino acid 179 N from the amino end include a probe having the nucleotide sequence as set forth in SEQ ID NO: 47 in the sequence list, which is capable of detecting the genes of 1 kind of SHV-type ESBL with amino acid 179 N from amino end including shv-8.

Suitable probes for detection of a SHV-type ESBL gene having amino acid 179 G from the amino end include a probe having the nucleotide sequence as set forth in SEQ ID NO: 48 in the sequence list, which is capable of detecting the genes of 1 kind of SHV-type ESBL with amino acid 179 G from amino end including shv-24.

The kits of the present invention may further comprise other control probes, such as surface chemistry control probe (such as a surface chemistry control probe having the nucleotide sequence as set forth in SEQ ID NO: 49), hybridization control probe (such as a hybridization control probe having the nucleotide sequence as set forth in SEQ ID NO: 50), the target of the said hybridization control probe (such as a nucleotide sequence having the nucleotide sequence as set forth in SEQ ID NO: 51), and negative control probe (such as a negative control probe having the nucleotide sequence as set forth in SEQ ID NO: 52).

The probes described herein can be immobilized on a carrier, such as a carrier made of silicon, glass slide modified with various functional groups or membranes with various functional groups, preferably glass slide with an aldehyde group.

In some embodiments, the probes described are immobilized in a microarray. "Microarray" and "array," as used interchangeably herein, comprises a surface with an array, preferably an ordered array, of putative binding (e.g., by hybridization) sites for a biochemical sample (target) which often have undetermined characteristics. In some embodiments, a microarray refers to an assembly of distinct probes immobilized at defined positions on a substrate.

Arrays may be formed on substrates fabricated with materials such as paper, glass, plastic (e.g., polypropylene, nylon, polystyrene), polyacrylamide, nitrocellulose, silicon, optical fiber or any other suitable solid or semisolid support, and configured in a planar (e.g., glass plates, silicon chips) or three dimensional (e.g., pins, fibers, beads, particles, microtiter wells, capillaries) configuration.

Probes forming the array may be attached to the substrate by any number of ways including, but not limiting to, (i) in situ synthesis (e.g., high-density oligonucleotide arrays) using photolithographic techniques; (ii) spotting/printing at medium to low density on glass, nylon or nitrocellulose; (iii) by masking and (iv) by dot-blotting on a nylon or nitrocellulose hybridization membrane, probes may also be non-covalently immobilized on the substrate by hybridization to anchors, by means of magnetic beads, or in a fluid phase such as in microtiter wells or capillaries.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995) 93:10614-10619). Arrays can also be printed by robotics onto glass, nylon (Ramsay, G., Nature Biotechnol. (1998), 16:40-44), polypropylene (Matson, et al., Anal Biochem. (1995), 224(1): 110-6), and silicone slides (Marshall, A. and Hodgson, J., Nature Biotechnol. (1998), 16:27-31). Other approaches to array assembly include fine micropipetting within electric fields (Marshall and Hodgson, supra), and spotting the polynucleotides directly onto positively coated plates. Methods such as those using amino propyl silicon surface chemistry are also known in the art.

One method for making microarrays is by making high-density nucleotide arrays. Techniques are known for rapid deposition of polynucleotides (Blanchard et al., *Biosensors & Bioelectronics,* 11:687-690). Other methods for making microarrays, e.g., by masking (Maskos and Southern, *Nuc. Acids. Res.* (1992), 20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

Other Components in the Kits

The kits of the present invention may also includes the reaction solutions for performing PCR and hybridization, and 50% dimethyl sulphoxide (DMSO) as the blank control of the hybridization reaction.

In some embodiments, the kit further comprises instructions for using the kits for detecting drug resistance genes. For example, the kit may comprise instruction on performing PCR reactions, hybridization reactions, and interpretation of hybridization results, and/or for carrying out methods described herein.

In some embodiments, the kit further comprises software for analyzing experimental results using kits or microarrays described herein.

Methods of Detecting Drug Resistance Genes in Gram-Negative Bacteria

Also provided are methods for detection of the drug resistance genes in gram-negative bacteria using the aforementioned kits for detection of the drug resistance genes in gram-negative bacteria.

In some embodiments, there is provided a method for detecting a drug resistance gene in gram-negative bacteria comprising: a) performing PCR using at least one primer pair that amplify a drug resistance gene of gram-negative bacteria; and b) hybridizing the amplified products with one or more probes there detect a drug resistance gene. In some embodiments, the drug resistance gene is selected from the group consisting of ten, shv, ctx-m-1-type, ctx-m-9-type, mox, cit, dha, acc, ebc, and fox.

The concentrations of the forward and reverse primer of the PCR primer pairs for detection of resistance genes in gram-negative bacteria can be equal or non-equal. For example, in some embodiments, one of the primers is tagged with a universal tagged sequence at its 5' end, and the concentration of the primer whose 5' end is linked with the said 5'-universal tagged sequence is 5-100 folds to the concentration of another primer. In some embodiments, the concentration of the tagged sequence is about 2.5 folds higher than that of the untagged sequence.

In some embodiments, the temperature cycles of the said PCR amplification includes two steps: the cycles in the first step are composed of denaturation, annealing and extension, comprising 10-25 cycles; the cycles in the second step are composed of denaturation and extension, including 10-25 cycles. In some embodiments, the denaturation temperature is 94° C., the annealing temperature is 50-70° C., preferably 55° C., and the extension temperature in the second step is 60-80° C., preferably is 70° C.

In some embodiments, the PCR is a multiplex asymmetric PCR. In the multiplex asymmetric PCR of the present invention, DNA polymerase, dNTP, $Mg^{2+}$ concentration and the compounds of the buffer are same as that in traditional PCR, and they can be optimized according to different reactions. The difference lies in the primers: one gene-specific primer is same as that in traditional PCR, while another gene-specific primer is added an oligonucleotide which is unrelated to the target sequence (such as the 5'-universal tagged sequence in Table 1). The concentrations of these two primers can be equal. The different gene-specific primers can be added the same tagged sequence (such as the 5'-universal tagged sequence in Table 1). The temperature cycles of one exemplary multiplex PCR include two steps (see Table 4): the first step is same as the traditional PCR, including denaturation, annealing and extension. The annealing temperature is adjusted according to Tm of the gene-specific primer; similarly, the extension time can be adjusted according to the length of the amplified fragment. After about 20 cycles, the reaction begins to perform the second step. The temperature cycles of the second step only include denaturation and extension, and the temperature of extension is about 70° C. In the first 20 cycles of amplification reaction, the primer pairs can perform the common PCR due to the annealing temperature is equivalent to Tm of the gene-specific primers. While in the latter 20 cycles of amplification, only the tagged gene-specific primer can anneal to the target, so that the single-stranded products are produced. The primers included in the kit for detection of the resistance genes in gram-negative bacteria are listed in Table 1.

The technique and the conditions of the hybridization between probes (Table 2) and PCR products are well-known by those of ordinary skills in the art. For example, the hybridization conditions are the follows: the median strict hybridization condition is at 50-60° C., 5×SSC for 1-2 hours, then washing in 2×SSC, 0.1% SDS (pH8.0), and then washing in distilled water at room temperature for 2 min. The highly strict hybridization condition is at a higher temperature (such as at 65-70° C.). For high specificity, preferably the lower salt concentration and/or higher temperature are used, such as the salt concentration is 0.02 mol/L to 0.15 mol/L, and the temperature is 50° C. to 65° C.

In one example in the present invention, the reverse hybridization technique is used, that is, the probes are immobilized on the carrier. The appropriate carrier is preferably silicon, glass slide with various functional groups and the membranes (such as nylon membrane, nitrocellulose membrane) that are derivated by various functional groups (such as nitryl group), and the most preferable is the glass slide with an aldehyde group. The target from the samples is labeled; preferably fluorescence labeled PCR products, and then hybridized with the probes immobilized on the glass slide after denaturation. For hybridization, the temperature, ion strength, pH and other buffers are selected according to the probe length, composition and the melting temperature of the hybrid (namely the combination of the labeled PCR products and the probes). Wahl et al, Proc. Natl. Acad. Sci. USA. 76 (1979) 3683-3687.

In order to detect the drug resistance genes in gram-negative bacteria, the hybridization signals of the targets and the probes are detected and analyzed by, such as, typically the fluorescence scanner, such as GenePix4000B scanner (Axon Instruments, Inc., CA, USA), and then analyzed the hybridization signals by an appropriate software (such as Genepix3.0).

The method of detection of resistance genes in gram-negative bacteria in the present invention and the kit thereof have the characteristics of high integration, high sensitivity, broad application, high specificity, reliability and high accuracy.

The present invention is further defined in the following examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Unless otherwise noted, the methods are conventional methods in the following examples.

Unless otherwise noted, the percent content in the following examples is the mass percent content.

EXAMPLES

Example 1

Detection of the Drug Resistance Genes in *K. pneumoniae* Using the Kit for Detection of Resistance Genes in Gram-Negative Bacteria in the Present Invention The detection object of the present kit is to detect the resistance genes of gram-negative bacteria *K. pneumoniae*, comprising tem, shv, ctx-m-1-type, ctx-m-9-type, mox, cit, dha, acc, ebc and fox. The detailed information of the primers and probes are listed in Table 1 and Table 2.

The primers and probes were synthesized by BioAsia Biotechnology Company Shanghai. The TAMRA of 5'-ends of some primers and the amino group of 5'-ends of some probes were also synthesized by BioAsia Biotechnology Company Shanghai.

The Preparation of Gram-Negative Bacteria Resistance Gene Detection Microarray

The preparation of the glass slides with aldehyde group: The glass slides were dipped into the washing solution, and incubated overnight. The slides were rinsed by tap water to wash out the acidic solutions, then washed by distilled water for three times and deionized water twice. The glass slides were dried by brief centrifugation, and dried at 110° C. for 15 min to dry the glass slides thoroughly. The glass slides were dipped into 1% APTES [(3-aminopropyl) triethoxysilane)] in 95% ethanol, and briefly shaking at room temperature for 1 hr. The treated glass slides were washed using 95% ethanol, and then washed twice. The clean glass slides were put into a vacuum drying oven, and vacuumized to the maximal scale (−0.08 Mpa to −0.1 Mpa), then closed the aerate valve, then treated at 110° C. for 20 min. Then the glass slides which were cooled to room temperature were dipped into 12.5% glutarlde solution (400 mL 12.5% glutarlde solution: 100 mL 50% glutarlde solution, 300 mL phosphate buffer (1 mol/L $NaH_2PO_4$ 30 mL, 2.628 g NaCl), pH 7.0), and briefly shaking at room temperature for 4 hr. The glass slides were taken from glutarlde solution, and washed in 3×SSC once, then washed in deionized water twice, then dried by brief centrifugation and dried at room temperature.

The preparation of glass slides immobilized with the probes (microarray): The probes in Table 2 were dissolved into 50% DMSO to the final concentration of 10 mol/L. Cartesian microarrayer (Cartesian Technologies, Inc., CA, USA) was used to spot the probes on the slides according to the panel in FIG. 1 (11 rows×9 columns). Each probe was printed triplicate, except that the surface chemistry control PBB-0201090 and hybridization control (EC) probe PBB-0204652 was printed six times. In FIG. 1, H means the surface chemistry control probe PBB-0201090, O means the blank control of hybridization 50% dimethyl sulphoxide (DMSO), P means hybridization control (EC) probe PBB-0204652, S means shv universal probe PBB-0201006, m238A means shv typing probe 238 A PBB-0201039, m238S means shv typing probe 238 S PBB-0201013, w238 means shv typing probe 238 G PBB-0201012, w240 means shv typing probe 240 E PBB-0201014, m240 means shv typing probe 240 K PBB-0201015, w35 means shv typing probe 35 L PBB-0201016 m35 means shv typing probe 35 Q PBB-0201017, w43 means shv typing probe 43 R PBB-0201029, m43 means shv typing probe 43 S PBB-0201030, w130 means shv typing probe 130 S pBB-0201044, m130 means shv typing probe 130 G pBB-0201045, w179 means shv typing probe 179 D pBB-0201040, m179A means shv typing probe 179 A pBB-0201041, m179N means shv typing probe 179 N pBB-0201042, m179G means shv typing probe 179 G pBB-0201043, 9 means ctx-m-9-type universal probe PBB-0201032, 1 means ctx-m-1-type universal probe PBB-0201033, T means tem universal probe pBB-0201027, M means mox universal probe PBB-0201031, C means cit universal probe PBB-0201025, D means dha universal probe PBB-0401031, A means acc universal probe PBB-0201035, F means fox universal probe PBB-0201063, E1 means ebc universal probe PBB-0401051, E2 means ebc universal probe PBB-0201036, E3 means ebc universal probe PBB-0201037, and N means negative control probe PBB-HC10.

The glass slide were incubated at room temperature overnight to dry the glass slide, then the glass slide was dipped into 0.2% SDS at room temperature twice for 2 min each time and shaking. The glass slide was washed using deionized water twice, and rinsed by deionized water once, then dried by centrifugation. The glass slide was transferred in $NaBH_4$ solution (1.0 g $NaBH_4$ in 300 mL 1×PBS, then adding 100 mL 100% ethanol), briefly shaking at room temperature for 5 min. The glass slide was washed using deionized water once, and washed twice for 1 min each time, then dried by centrifugation.

Bacteria Culture and Nucleic Acid Extraction

Three gram-negative bacteria in Table 3 were tested. The in vitro antimicrobial susceptibility result was obtained according to the standard method of Clinical and Laboratory Standards Institute (CLSI).

TABLE 3

The information of the tested strains

| Strain No. | Origin | Species[b] | The in vitro antimicrobial susceptibility test/MIC[a] (µg/ml) | | | | | | Sequencing result |
|---|---|---|---|---|---|---|---|---|---|
| | | | CAZ[a] | CAZ + CLA | CTX | CTX + CLA | FOX | IMP | |
| E298 | Beijing Hospital | *K. pneumoniae* | ≧128 | ≧128 | ≧128 | ≧128 | ≧128 | <0.5 | tem-1, ctx-m-3, dha-1 |
| BJ-7 | Beijing Hospital | *K. pneumoniae* | 32 | 1 | 64 | ≦0.25 | 8 | <0.5 | shv-2 |
| BJ-35 | Beijing Hospital | *K. pneumoniae* | 4 | <0.5 | 8 | <0.25 | 2 | <0.5 | shv-1 |

Note:

[a]antibiotics: CAZ—ceftazidime; CLA—clavulanate (the fixed concentration is 4 µg/ml); CTX—cefotaxime; FOX—cefoxitin; IMP—imipenem.

[b]*K. pneumoniae*: *Klebsiella pneumoniae*.

The bacteria were inoculated on MH (Mueller Hinton Agar Medium) agar in ultra-clean bench to isolate single colonies, and converted the plate in the incubation oven at 35° C. for 24 h.

One single colony was picked from the culturing MH plate, and then 100 μl×TE was added. The centrifugation tube was incubated into the water at 95° C. for 5 min, then placed at 4° C. ready for use.

Multiplex Asymmetric PCR

The reaction system of multiplex asymmetric PCR was as follows: 1×MasterMix (Tianwei Times Biotechnology Company Beijing); ten of gene-specific primer pairs in Table 1 except 5'-end universal sequence (the tagged primers 0.1 μmol/L and the untagged primers 0.04 μmol/L); 1 μL of lysate or 1 μL of sterile water (as the blank control). The total volume is 25 μL.

PCR was performed in PTC-200 (MJ Research Inc.) cycler, and the multiplex asymmetric PCR amplification program was listed in Table 4.

(CapitalBio Company, Beijing). The detection wavelength was 555 nm. Laser power was fixed at 80%, and photomultiplier tube (PMT) is 80%.

Analysis of the Results

Figure 2:
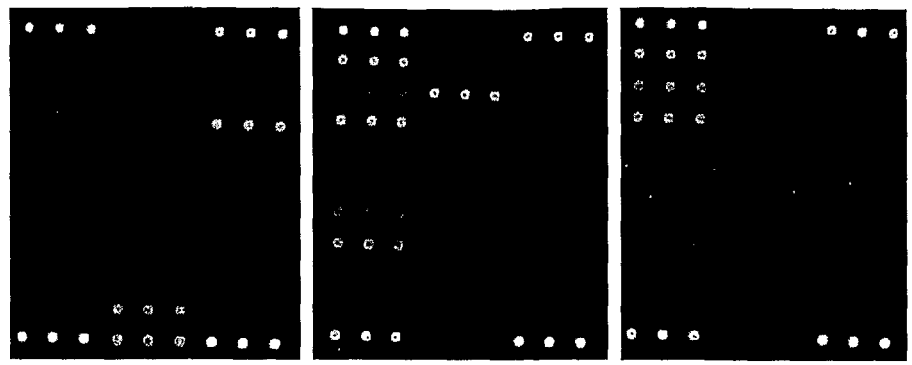
FIG. 2 provides hybridization results for detection of drug resistance genes in *K. pneumoniae* using an exemplary kit of the present invention.

The hybridization results are shown in FIG. 2. E298 contains tem, ctx-m-3-like and dha-1 genes detected by the microarray, which is consistent to the sequencing results. The results show that this isolate is resistant to the third generation cephalosporin and cefoxitin, and not inhibited by clavulanate, which is consistant to the in vitro antimicrobial susceptibility results. BJ-7 contains shv-2 gene detected by the microarray, which is consistent to the sequencing result. The results show that this isolate is resistant to the third generation cephalosporin, but susceptible to cefoxitin and inhibited by clavulanate, which is consistent with the in vitro antimicrobial susceptibility results. BJ-35 contains shv-1 gene detected by the microarray, which is consistent with the sequencing result. The results show that this isolate is susceptible to the

TABLE 4

| The amplification cycles of multiplex asymmetric PCR | | | | | | | |
|---|---|---|---|---|---|---|---|
| teperature (° C.) | 94 | 94 | 59 | 72 | 94 | 70 | 72 | 4 |
| time (s) | 600 | 1 | 60 | 90 | 1 | 120 | 300 | — |
| Cycle number | 1 | 20 | | | 20 | | 1 | 1 |
| Note | predenatureation | The first run of PCR amplification | | | The second t run of PCR amplification | | Extension | Stop |

Microarray Hybridization and Data Analysis

The preparation of the hybridization mixture is showed in Table 5.

TABLE 5

| The hybridization mixture | | |
|---|---|---|
| Component | Final concentration | Volume (μl) |
| H$_2$O | / | 1.0 |
| 20×SSC | 2x | 1.8 |
| 50×Denhardt's | 5x | 1.8 |
| 50% dextran | 10% | 3.6 |
| 4% SDS | 0.4% | 1.8 |
| MAPCR products | / | 8.0 |
| Total | / | 18.0 |

200 μl distilled water was added into the HYBRICASSETTES™ hybridization cassettes CapitalBio Company, Beijing) to prevent the evaporation of the hybridization mixture, then the glass slide with immobilized the probes on the surface and the SMARTCOVER™ coverslip CapitalBio Company, Beijing) were put into the hybridization cassettes. The hybridization solution was heated at 95° C. for 5 min to denature the PCR products thoroughly and then cooled down rapidly on ice. 13 μL of mixture was applied into the slide through the pore on the coverslip, and then covered the cassette to hybridize at 54° C. for 90 min. The microarray was taken out and dipped into 2×SSC, 0.2% SDS solution, briefly shaking at room temperature for 5 min. The microarray was washed using deionized water twice for 2 min each time, and then dried by centrifugation.

The fluorescent signals on microarray were detected using LUXSCAN™ 10 K/B confocal scanner and its software third generation cephalosporin and cefoxitin, also inhibited by clavulanate, which is consistent with the in vitro antimicrobial susceptibility results.

The results obtained by the present method are highly consistent with the results of traditional methods (such as MIC). Thus the kit for detection of drug resistance genes in gram-negative bacteria in the present invention can be used to specifically detect the resistance genes in the prevalent gram-negative bacteria *K. pneumoniae*.

Example 2

Figure 3:
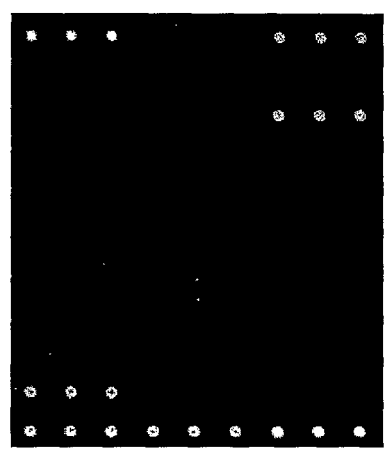
FIG. 3 provides hybridization results for detection of drug resistance genes in *E. coli* using an exemplary kit of the present invention.

Detection of the Resistance Genes in *E. coli* Using the Gram-Negative Bacteria Resistance Genes Detection Kit in the Present Invention The resistance genes in *E. coli* Z302 were detected using the microarray in FIG. 1 according to the method in Example 1. The results are showed in Table 6 and FIG. 3, indicating that the isolate contains tem, ctx-m-9-like and cit group of genes by detection of microarray, which is consistent with the sequencing results, showing that the isolate was resistant to the third generation cephalosporin and cefoxitin, and not inhibited by clavulanate, which is consistent with the traditional in vitro antimicrobial susceptibility results (MIC). Thus the kit for detection of resistance genes in gram-negative bacteria in the present invention can be used to specifically detect the resistance genes in the prevalent gram-negative bacteria *E. coli*.

TABLE 6

The information of the tested strains

| | | | The in vitro antimicrobial susceptibility test/MIC$^a$ (μg/ml) | | | | | | |
|---|---|---|---|---|---|---|---|---|---|
| Strain No. | Origin | Species | CAZ$^a$ | CAZ + CLA | CTX | CTX + CLA | FOX | IMP | Sequencing result |
| Z302 | Beijing Tiantan Hospital | E. coli | ≧128 | 64 | ≧128 | 64 | ≧128 | 4 | tem-1, cmy-2, ctx-9 |

Note:
$^a$antibiotics: CAZ—ceftazidime; CLA—clavulanate (the fixed concentration is 4 μg/ml); CTX—cefotaxime; FOX—cefoxitin; IMP—imipenem.

Example 3

Figure 4:
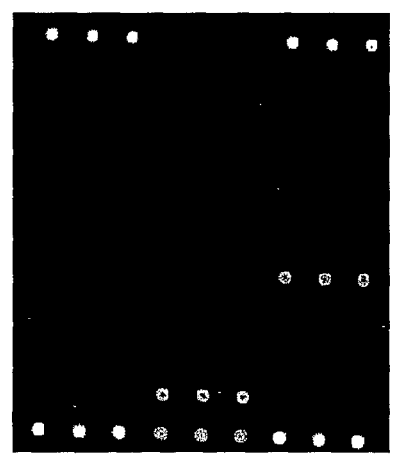
FIG. 4 provides hybridization results for detection of drug resistance genes in *E. cloacae* using an exemplary kit of the present invention.

Detection of Drug Resistance Genes in E. cloacae Using the Gram-Negative Bacteria Resistance Genes Detection Kit in the Present Invention The resistance genes in E. cloacae TR3104 were detected using the microarray in FIG. 1 according to the method in example 1. The results are showed in Table 7 and FIG. 4, indicating that the isolate contains tem, ctx-m-3-like and chromosomal ampC genes by detection of microarray, which is with the sequencing results, showing the isolate is resistant to the third generation cephalosporin and cefoxitin, which is consistent with the traditional in vitro antimicrobial susceptibility results (MIC). Thus the kit for detection of resistance genes in gram-negative bacteria in the present invention can be used to specifically detect the resistance genes in the prevalent gram-negative bacteria E. cloacae.

TABLE 7

The information of the tested strains

| | | | The in vitro antimicrobial susceptibility test/MIC$^a$ (μg/ml) | | | | | | Sequencing |
|---|---|---|---|---|---|---|---|---|---|
| Strain No. | Origin | Species | CAZ$^a$ | CAZ + CLA | CTX | CTX + CLA | FOX | IMP | result |
| TR3104 | Beijing Tiantan Hospital | E. coli | 4 | 1 | 64 | 1 | ≧256 | 4 | tem-1, AmpC, ctx-3 |

Note:
$^a$antibiotics: CAZ—ceftazidime; CLA—clavulanate (the fixed concentration is 4 μg/ml); CTX—cefotaxime; FOX-cefoxitin; IMP-imipenem.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A kit for detecting one or more drug resistance genes in a gram-negative bacteria, comprising at least five primer pairs selected from the group consisting of SEQ ID NOS: 2 and 3, SEQ ID NOS: 4 and 5, SEQ ID NOS: 6 and 7, SEQ ID NOS: 8 and 9, SEQ ID NOS: 10 and 11, SEQ ID NOS: 12-13, SEQ ID NOS: 14-15, SEQ ID NOS: 16-17, SEQ ID NOS: 18-19 or SEQ ID NOS: 20-21 primer pairs for amplification of a drug resistance gene, wherein the drug resistance gene is selected from the group consisting of tem, shv, ctx-m-1-type, ctx-m-9-type, mox, cit, dha, acc, ebc, and fox.

2. The kit of claim 1, wherein the gram-negative bacteria is selected from the group consisting of E. coli, K pneumoniae, and E. cloacae.

3. The kit of claim 1, wherein the kit further comprises one or more probes for detecting at least one drug resistance gene selected from the group consisting of tem, shv, ctx-m-1-type, ctx-m-9-type, mox, cit, dha, acc, ebc, and fox.

4. The kit of claim 3, wherein the kit comprises at least two probes having the sequence as set forth in SEQ ID NOS:22-52.

5. The kit of claim 4, wherein the kit comprises at least five probes having the sequence as set forth in SEQ ID NOS:22-52.

6. The kit of claim 3, further comprising one or more control probes, wherein the control probe is selected from the group consisting of: surface chemistry control probe, hybridization control probe, and negative control probe.

7. The kit of claim 3, wherein the probes are immobilized on a carrier.

8. The kit of claim 1, further comprising solutions for PCR reaction or solution for hybridization reaction.

9. The kit of claim 1, further comprising an instruction for using the kit.

10. A microarray for detection of a drug resistance gene in gram-negative bacteria, comprising at least one probe for a gene selected from the group consisting of tem, shv, ctx-m-1-type, ctx-m-9-type, mox, cit, dha, acc, ebc, and fox, wherein the microarray comprises at least two probes having the sequence as set forth in SEQ ID NOS:22-52.

11. The microarray of claim 10, wherein the microarray comprises at least five probes having the sequence as set forth in SEQ ID NOS:22-52.

12. The microarray of claim 10, further comprising one or more control probes, wherein the control probe is selected from the group consisting of: surface chemistry control probe, hybridization control probe, negative control probe.

13. The microarray of claim 12, wherein the probes are about 15-35 nucleotides.

14. A method for detecting a drug resistance gene in gram-negative bacteria comprising: a) performing PCR using at least one primer pair that amplify a drug resistance gene of gram-negative bacteria; and b) hybridizing the amplified products with at least two probes having the sequence as set forth in SEQ ID NOS:22-52 to detect the drug resistance gene, wherein the drug resistance gene is selected from the group consisting of tem, shv, ctx-m-1-type, ctx-m-9-type, mox, cit, dha, acc, ebc, and fox.

15. The method of claim 14, wherein the PCR is multiplex asymmetric PCR.

16. The method of claim 14, wherein the concentration of the two primers in each pair are equal.

17. The method of claim 16, wherein one of the primers in each pair comprises a universal tag sequence at the 5' end, and wherein the concentration of the tagged primer is about 5-100 folds of that of the untagged primer.

18. The method of claim 17, wherein the PCR comprises 10-25 cycles of denaturation, annealing, and extension, followed by 10-25 cycles of denaturation and extension.

* * * * *